US009932302B1

(12) United States Patent
Jackson-Ayotunde et al.

(10) Patent No.: US 9,932,302 B1
(45) Date of Patent: Apr. 3, 2018

(54) N-PHENYL AND N-BENZYL ENAMINONES AND METHODS FOR USING SAME

(71) Applicants: Patrice L. Jackson-Ayotunde, Salisbury, MD (US); Tawes Harper, East New Market, MD (US)

(72) Inventors: Patrice L. Jackson-Ayotunde, Salisbury, MD (US); Tawes Harper, East New Market, MD (US)

(73) Assignee: University of Maryland Eastern Shore, Princess Anne, MD (US)

( * ) Notice: Subject to any disclaimer, the term of this patent is extended or adjusted under 35 U.S.C. 154(b) by 0 days.

(21) Appl. No.: 14/519,679

(22) Filed: Oct. 21, 2014

Related U.S. Application Data

(60) Provisional application No. 61/893,652, filed on Oct. 21, 2013.

(51) Int. Cl.
| | | |
|---|---|---|
| A01N 41/06 | (2006.01) |
| A61K 31/18 | (2006.01) |
| C07C 311/29 | (2006.01) |
| C07C 235/54 | (2006.01) |
| C07C 233/76 | (2006.01) |
| C07C 311/13 | (2006.01) |
| C07C 311/20 | (2006.01) |
| A61J 1/05 | (2006.01) |

(52) U.S. Cl.
CPC ............. *C07C 311/29* (2013.01); *A61J 1/05* (2013.01); *C07C 233/76* (2013.01); *C07C 235/54* (2013.01); *C07C 311/13* (2013.01); *C07C 311/20* (2013.01); *C07C 2101/16* (2013.01)

(58) Field of Classification Search
CPC ........ A61K 31/18; A61K 8/42; A61K 31/165; C07C 2101/14; C07C 311/29; C07C 309/00
See application file for complete search history.

(56) References Cited

U.S. PATENT DOCUMENTS 6,579,857 B1 * 6/2003 Lind et al. ...................... 514/46

FOREIGN PATENT DOCUMENTS

WO WO 9317678 A1 * 9/1993 ........... C07C 45/512

OTHER PUBLICATIONS

Jackson, Howard University, Graduate School, Department of Pharmaceutical Sciences, Apr. 7, 2009, referred herein as "Jackson-1".*
Jakson, Bioorganic & Medicinal Chemistry 17 (2008) 133-140, referred herein as "Jackson-2".*
Shadabul et al, Drug Development and Industrial Pharmacy, 2012; 38(4): 387-411.*

* cited by examiner

*Primary Examiner* — Jean P Cornet
(74) *Attorney, Agent, or Firm* — Hodgson Russ LLP

(57) ABSTRACT

The present disclosure provides compounds, compositions, and methods for use of the compounds. The compounds are N-phenyl or N-benzyl enaminones. The compositions can be pharmaceutical compositions. For example, the compounds/compositions are used in treating seizure disorders. The methods entail administering a composition comprising one or more of the compounds to a subject in need thereof. Articles of manufacture comprising one or more of the compounds/compositions are also provided.

13 Claims, 2 Drawing Sheets

Figure 1. Anticonvulsant N-aryl Sulfonamide and Benzmide Enaminones

Scheme 1. General Synthetic Route for Generation of N-Aryl Sulfonamide and Benzamide Enaminones

N-PHENYL AND N-BENZYL ENAMINONES AND METHODS FOR USING SAME

CROSS REFERENCE TO RELATED APPLICATIONS

This application claims priority to U.S. provisional patent application No. 61/893,652, filed Oct. 21, 2013, the disclosure of which is incorporated herein by reference.

FIELD

This disclosure relates generally to the area of seizure disorders. More particularly, the disclosure relates to enaminones and their use for seizure disorders.

BACKGROUND OF THE INVENTION

Epilepsy is a chronic syndrome characterized by brief spontaneous recurrent seizures. It is known that about 1 in every 26 Americans will be diagnosed with epilepsy at some point in their lifetime. Despite the use of available antiepileptic drugs, 25-30% of patients do not achieve seizure control with existing medications. Therefore, there is an ongoing and unmet medical need for new antiepileptic agents with improved efficacy and safety profiles for reduction in frequency, intensity, and duration of seizures.

SUMMARY

In aspects, the present disclosure provides compounds, compositions comprising the compounds, and methods for using the compounds and compositions. For example, the compounds/compositions are used in methods of prophylaxis and/or therapy of seizures. The compounds are novel N-phenyl or N-benzyl enaminones. The compounds may be in the form of pharmaceutically acceptable salts of the compounds. The compositions include pharmaceutical formulations comprising one or combinations of the compounds and are suitable for administration to a human subject in need thereof. In an embodiment, the present disclosure provides a composition comprising one or more of the instant compounds and a pharmaceutically acceptable carrier.

In various embodiments, the compounds have the following structure:

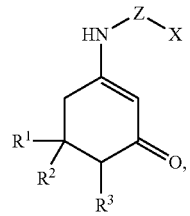

where Z is —C(O)— or —S(O)$_2$—, X is a phenyl group or a benzyl group and the phenyl group is substituted at least at the para position with a C$_1$-C$_2$ perfluoroalkyl group or C$_1$-C$_2$ perfluoroalkoxy group. R$^1$ and R$^2$ are independently selected from H and C$_1$-C$_2$ alkyl groups, with the proviso that if R$^1$ or R$^2$ is a C$_2$ alkyl group the other R group is H. R$^3$ is optional and is selected from —C(O)R$^4$ groups and R$^4$ is a C$_1$-C$_4$ alkyl group. The phenyl group may be substituted at the ortho position(s), meta position(s), or a combination thereof of the phenyl group with one to three groups selected from halogen group, C$_1$-C$_2$ alkyl group, C$_1$-C$_2$ alkoxy group, C$_1$-C$_2$ perfluoroalkyl group, C$_1$-C$_2$ perfluoroalkoxy group, and combinations thereof. The benzyl group may be substituted at the ortho position(s), meta position(s), para position, or a combination thereof of the benzyl group with one to three groups selected from halogen, C$_1$-C$_2$ alkyl group, C$_1$-C$_2$ alkoxy group, C$_1$-C$_2$ perfluoroalkyl group, C$_1$-C$_2$ perfluoroalkoxy group, and combinations thereof.

In various embodiments, the compounds have the following structure:

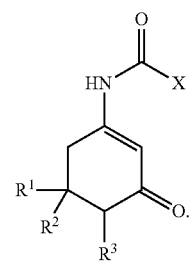

For example, the compounds have the following structure:

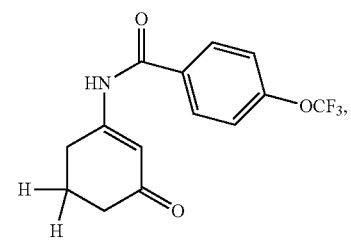

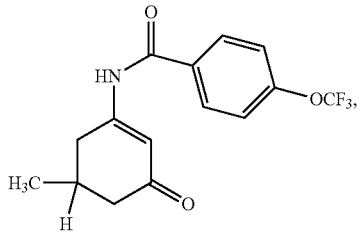

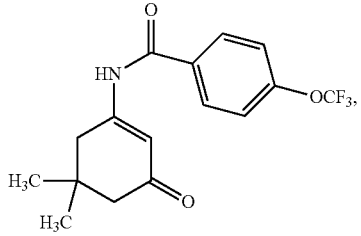

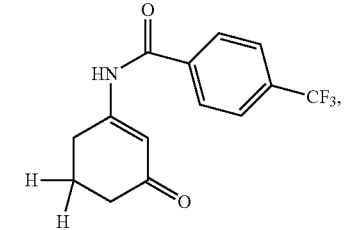

-continued

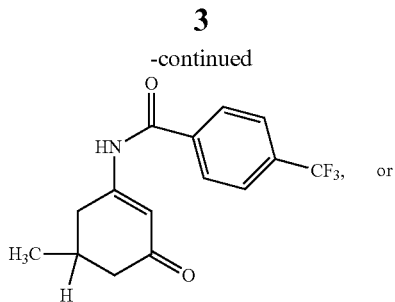

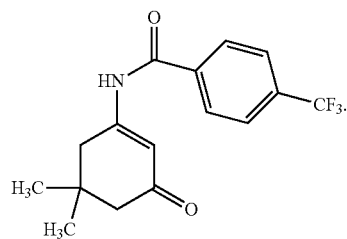

In various embodiments, the compounds have the following structure:

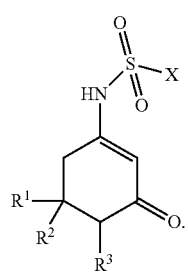

For example, the compounds have the following structure:

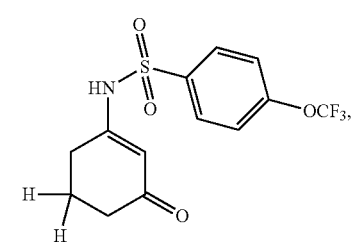

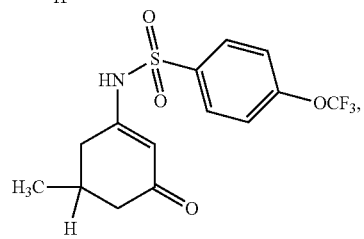

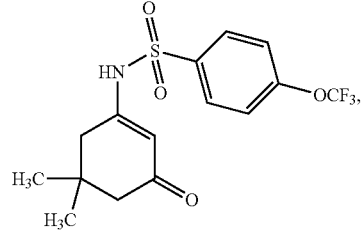

-continued

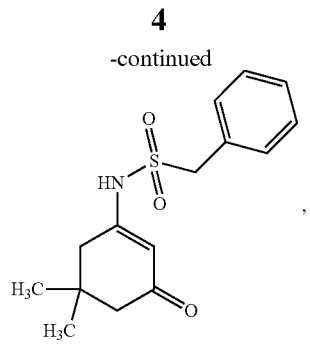

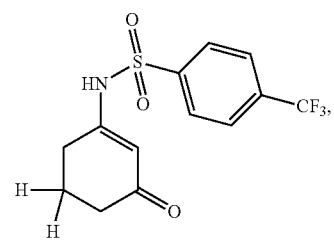

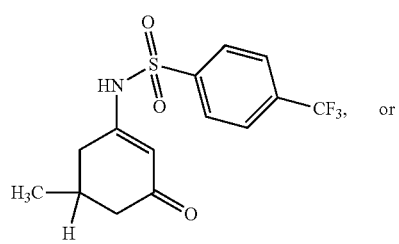

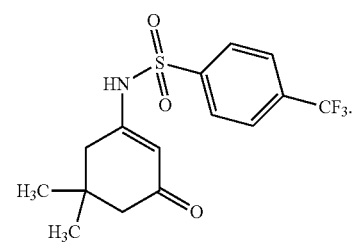

In an embodiment, the disclosure provides administering to a subject in need thereof a composition comprising one or a combination of compounds disclosed herein such that a seizure disorder in an individual is treated. In embodiments, the administration results in a reduction in the severity and/or frequency and/or duration of seizures experienced by the individual. In embodiments, the seizures comprise a focal seizure, a generalized seizure, or a combination thereof. In embodiments, the individual is an individual diagnosed with or suspected of having epilepsy.

Given the benefit of the present disclosure those skilled in the art will recognize that the compositions comprising one or more compounds described herein can be administered to the individual using any suitable method, formulation, route, and/or dosing regimen. In embodiments, the compositions are formulated for and may be administered by an oral or intravenous route. In embodiments, the compositions comprise pharmaceutical formulations that comprise a pharmaceutically acceptable carrier or excipient. In embodiments, the compositions are provided in the form of a tablet or capsule.

In an aspect, the disclosure includes an article of manufacture which comprises packaging and at least one container, where the container contains a composition comprising one or a combination of compounds described herein, the article further comprises printed material, the printed material providing an indication that the composition is for use in treatment of a seizure disorder, which can include, but is not limited to, any epileptic condition.

DETAILED DESCRIPTION OF THE INVENTION

Figure 1:
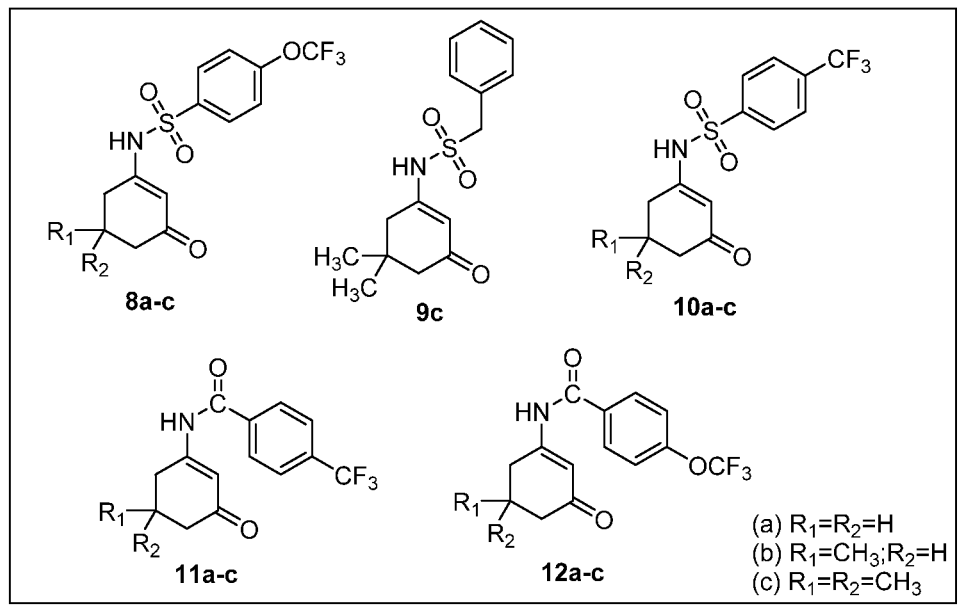
FIG. 1 provides a depiction of examples of anticonvulsant N-phenyl sulfonamide and benzamide compounds of this disclosure.

The disclosure provides novel enaminones (e.g., N-benzyl and N-phenyl enaminones) and compositions comprising one or more of the enaminones. The compounds/compositions are useful for medicinal interventions in the area of seizure disorders.

The instant compounds block partial seizures in the therapy-resistant 6 Hz "psychomotor' rodent test with limited to no observed neurotoxicity. Results from advanced focal seizure models further demonstrate the partial seizure activity of the compounds.

As used herein, the term "alkyl group", unless otherwise stated, refers to branched or unbranched hydrocarbon group (e.g., an —R group). Examples of such alkyl groups include methyl groups, ethyl groups, propyl groups, butyl groups, isopropyl groups, tert-butyl groups, and the like. For example, the alkyl group is a $C_1$ to $C_2$ alkyl group or a $C_1$ to $C_4$ alkyl group. The alkyl group can be unsubstituted or substituted with various substituents as described herein (e.g., perfluoroalkyl groups).

As used herein, the term "alkoxy group", unless otherwise stated, refers to an —OR group, where R is a hydrocarbon group (e.g., an alkyl group). Examples of such alkoxy groups include methoxy groups, ethoxy groups, and the like. For example, the alkoxy group is be a $C_1$ to $C_2$ alkoxy group. The alkoxy group can be unsubstituted or substituted with various substituents as described herein (e.g., perfluoroalkoxy groups).

In an aspect, the present disclosure provides N-phenyl and N-benzyl enaminones. The N-phenyl and N-benzyl enaminones can be benzamides or sufonamides.

In an embodiment, the compound has the following structure:

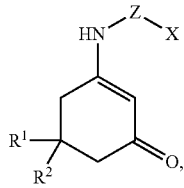

(Structure I)

where Z is —C(O)— or —S(O)$_2$—, X is an phenyl group or a benzyl group, and $R^1$ and $R^2$ are independently selected from H and $C_1$-$C_2$ alkyl groups. In the case where $R^1$ or $R^2$ is a $C_2$ alkyl group, the other R group is H.

The phenyl group is substituted at least at the para position with a $C_1$-$C_2$ perfluoroalkyl group or $C_1$-$C_2$ perfluoroalkoxy group. The phenyl group is, optionally, substituted with one, two or three groups at the ortho position(s) and/or meta position(s), or a combination of ortho and meta positions. The phenyl group is optionally substituted with one or more groups such as, for example, halogens (chloro groups, fluoro groups, and/or iodo groups), $C_1$-$C_2$ alkyl groups, $C_1$-$C_2$ alkoxy groups, $C_1$-$C_2$ perfluoroalkyl groups, $C_1$-$C_2$ perfluoroalkoxy groups, or combinations thereof.

Examples of phenyl group substituents and combinations of substituents include, but are not limited to, 2-Trifluoromethyl, 2-Trifluoromethoxy, 2,4-Bis(Trifluoromethyl), 2,5-Bis(Trifluoromethyl), 2,6-Bis(Trifluoromethyl), 2-Fluoro-4-(Trifluoromethyl), 2-Fluoro-5-(Trifluoromethyl), 2-Fluoro-6-(Trifluoromethyl), 3-Trifluoromethyl, 3-Trifluoromethoxy, 3,5-Bis(Trifluoromethyl), 3-Fluoro-4-(Trifluoromethyl), 3-Fluoro-4-(Trifluoromethyl), 3-Fluoro-5-(Trifluoromethyl), 3-Chloro-2-Fluoro-5-(Trifluoromethyl), and 5-Chloro-2-(Trifluoromethyl).

The benzyl group is optionally substituted. For example, the benzyl group is substituted with one, two, or three groups in the ortho positions(s) and/or meta position(s) and/or para position, or a combination of ortho, meta, and para positions. The benzyl group is substituted with one or more groups such as, for example, halogens (chloro groups, fluoro groups, and/or iodo groups), $C_1$-$C_2$ alkyl groups, $C_1$-$C_2$ alkoxy groups, $C_1$-$C_2$ perfluoroalkyl groups, $C_1$-$C_2$ perfluoroalkoxy groups, or combinations thereof.

Examples benzyl group substituents and combinations of substituents include, but are not limited to, 2-Trifluoromethyl, 2-Trifluoromethoxy, 2,4-Bis(Trifluoromethyl), 2,5-Bis(Trifluoromethyl), 2,6-Bis (Trifluoromethyl), 2,4-Dimethyl, 2-Fluoro-3-(Trifluoromethyl), 2-Fluoro-4-(Trifluoromethyl), 2-Fluoro-5-(Trifluoromethyl), 2-Fluoro-6-(Trifluoromethyl), 3-Trifluoromethyl, 3-Trifluoromethoxy, 3,5-Bis(Trifluoromethyl), 3-Fluoro-4-(Trifluoromethyl), 3-Fluoro-4-(Trifluoromethyl), 3-Fluoro-5-(Trifluoromethyl), 3-Chloro-2-Fluoro-5-(Trifluoromethyl), 4-Ethyl, 4-Ethoxy, 4-Fluoro-2-(Trifluoromethyl), 4-Methyl-3-(Trifluoromethyl), and 5-Chloro-2-(Trifluoromethyl).

The cyclohexenone ring of the compound may be substituted at the 6 position. Accordingly, in an embodiment, the compound has the following structure:

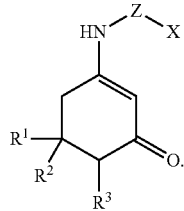

(Structure II)

In this embodiment, $R^3$ is selected from —C(O)$R^4$ groups and $R^4$ is a $C_1$-$C_4$ alkyl group. $R^1$, $R^2$, Z and X are as described herein.

In an embodiment the compound has the following structure:

(Structure III)

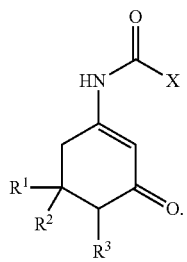

$R^1$, $R^2$, and X are as described herein. $R^3$ is optional and is as described herein. For example, the compound has any of the following structures:

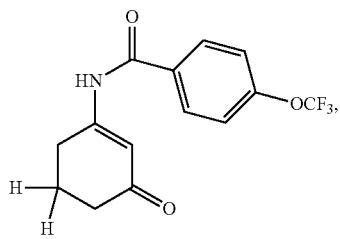

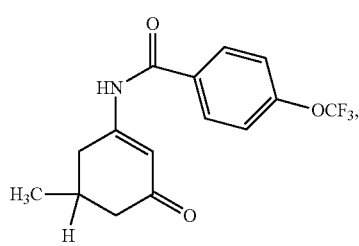

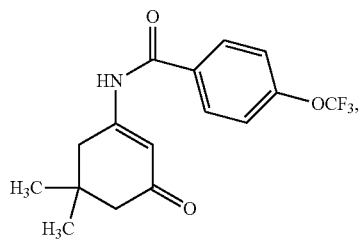

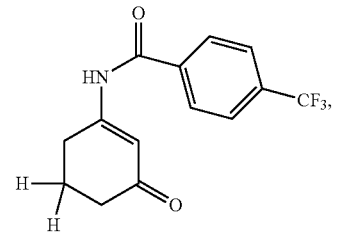

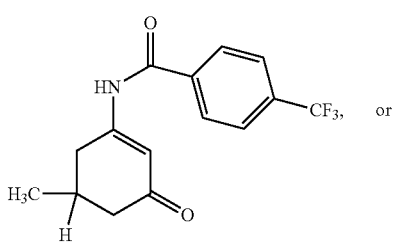 or

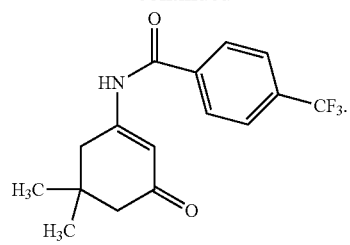

In an embodiment, the compound has the following structure:

(Structure IV)

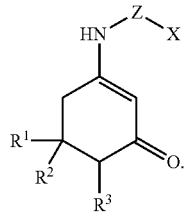

In this embodiment, $R^1$ and $R^2$ are both methyl or one of $R^1$ and $R^2$ is hydrogen and other is methyl. $R^3$ is optional and is as described herein. Z is —C(O). X is as described herein. For example, X is a phenyl group substituted with at least an electron withdrawing group in the para position.

In an embodiment the compound has the following structure:

(Structure V)

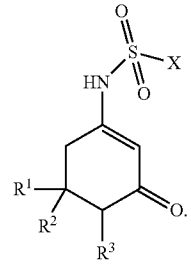

$R^1$, $R^2$, and X are as described herein. $R^3$ is optional and is as described herein. For example, the compound has any one of the following structures:

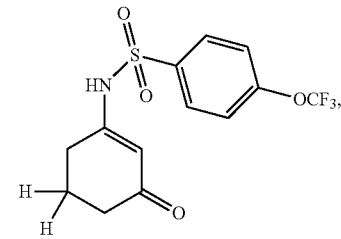

-continued

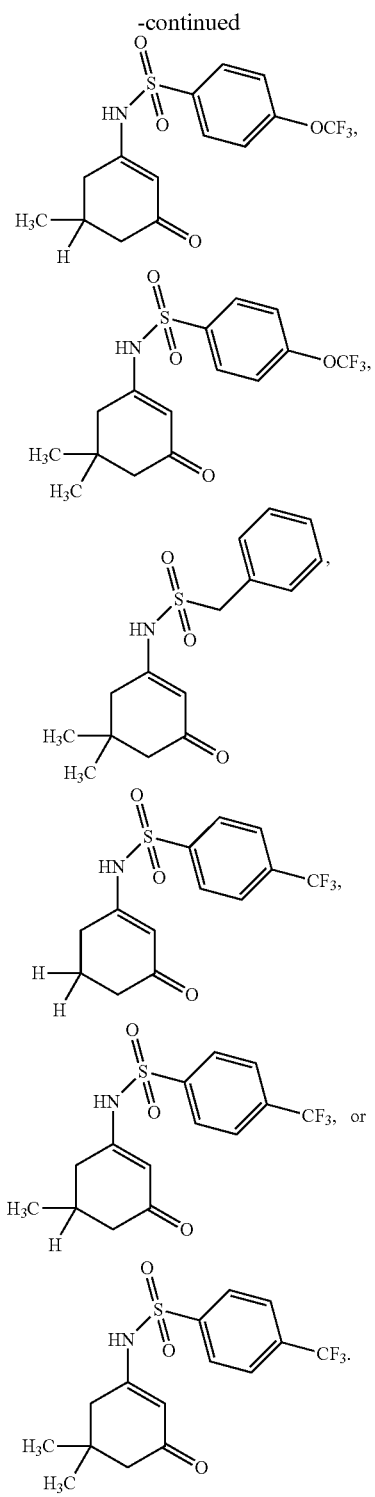

The present disclosure includes all possible stereoisomers and geometric isomers of the N-phenyl or N-benzyl enaminones (e.g., a compound having Structure (I) to (V)). The present disclosure includes both racemic compounds and optically active isomers. When the enaminone is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. In situations where tautomers of the enaminones are possible, the present disclosure includes all tautomeric forms of the compounds. Various crystalline forms of the compounds (including any polymorphs) are included in the present invention. Some of the compounds may form solvates with water (i.e., hydrates) or common organic solvents, and such solvates are also included in the present disclosure.

The N-phenyl or N-benzyl enaminone compounds may be salts. For use in medicinal applications, the salts of the compounds refer to non-toxic "pharmaceutically acceptable salts." Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In particular, the benzamide and sulfonamide groups are weakly acidic functional groups (benzamides have weaker acidity than sulfonamides). Therefore, in both cases a strong alkaline metal salt will be suitable for formation of pharmaceutically acceptable salts (e.g., sodium or potassium salts).

The compounds can be synthesized by amination of β-diketones to provide an enaminone intermediates, followed by N-sulfonylation or N-acylation of the enaminone intermediates with aromatic sulfonyl or acyl chlorides (e.g., in a base-catalyzed reaction). The β-diketones can be synthesized by condensation of an unsaturated ester and an acetylacetonate. For example, in the amination reaction a mono-methyl, dimethyl, or unsubstituted diketone is reacted with ammonium acetate and acetic acid in a 1:2 molar ratio utilizing anhydrous benzene as the solvent to form an enaminone intermediate. After refluxing with a Dean-Stark trap, the enaminone intermediate undergoes a base-catalyzed reaction with a selected substituted (e.g., para-substituted) benzene acyl or sulfonyl chloride to generate the desired enaminone compound.

In an aspect, this disclosure provides compositions comprising one or more of the compounds disclosed herein. The compositions can be compositions suitable for use as pharmaceuticals (i.e., pharmaceutical compositions).

The compositions comprise any one or any combination of the compounds, including, but not limited to, any 1, 2, 3, 4, 5, 6, 7, 8, 9, 10, 11, 12, 13, or 14, or more of such compounds. In embodiments, any one or any combination of the compounds can be excluded from a composition.

The N-phenyl or N-benzyl enaminone compound (e.g., a compound having the structure (I) to (V)) may be a prodrug. The compositions may comprise a prodrug of the N-phenyl or N-benzyl enaminone compound. The methods of using the N-phenyl or N-benzyl enaminone compound may use a prodrug of the compound. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B.

Silverman, "The Organic Chemistry of Drug Design and Drug Action," Academic Press, San Diego, chapter 8, (1992); K. M. Hillgren et al., Med. Res. Rev., 15, 83 (1995)). For example, $R^3$ is derivatized to form a prodrug.

Compositions comprising the compounds for performing any method of this disclosure may be prepared by mixing one or more of the compounds with, for example, any suitable pharmaceutically acceptable carriers, excipients and/or stabilizers. Suitable pharmaceutically acceptable carriers, excipients and/or stabilizers are known in the art. Some examples of compounds such as pharmaceutically acceptable carriers, excipients and/or stabilizers suitable for mixing with the compound(s) can be found in: *Remington: The Science and Practice of Pharmacy* (2005) 21st Edition, Philadelphia, Pa. Lippincott Williams & Wilkins.

In aspect, the present disclosure provides methods of using the compounds/compositions disclosed herein. For example, the compounds/compositions are used as pharmaceutical agents. The compounds/compositions may be used in combination with other medications (e.g., anti-seizure medications).

In embodiments, the present disclosure relates to compounds that are active in a 6 Hz model. In certain embodiments, the compounds are active in a 6 Hz model, but not active in one or a combination of other models described herein.

A composition can be administered to any individual in need thereof. In embodiments, the subject to whom a composition of this disclosure is administered is undergoing, has experienced, and/or is at risk for experiencing a seizure, and thus may be diagnosed with or be suspected of having any seizure disorder. In embodiments, the seizure disorder is selected from the group consisting of epilepsy, epilepsy related disorders, and chemically-induced seizure disorders. In embodiments the individual in need is a human or a non-human animal, the latter being applicable for veterinary purposes. In one embodiment, the non-human animal is a canine animal.

Epilepsy and related disorders and their attendant seizure symptoms are well characterized in the art. In this regard, the present disclosure is expected to be pertinent to any subject, such as an adult human, child, or infant, who experiences one or more seizures. In an embodiment, the seizures can comprise tremors. Suitable examples of seizure disorders include, but are not limited to, epilepsy (including, but not limited to, localization-related epilepsies, generalized epilepsies, epilepsies with both generalized and/or local seizures, and the like), seizures associated with Lennox-Gastaut syndrome, seizures as a complication of a disease or condition (such as seizures associated with encephalopathy, phenylketonuria, juvenile Gaucher's disease, Unvericht-Lundborg's progressive myoclonic epilepsy, stroke, head trauma, stress, hormonal changes, drug use or withdrawal, alcohol use or withdrawal, sleep deprivation, fever, infection, brain cancer, and the like), essential tremor, restless limb syndrome, and the like. In embodiments, the disorder is selected from epilepsy (regardless of type, underlying cause or origin), essential tremor syndrome, or restless limb syndrome. In embodiments, the seizure disorder is a disease or condition that is mediated by elevated persistent sodium current and/or other neural ionotropic abnormalities.

As will be recognized in the art, a characteristic that distinguishes categories of seizures is whether the seizure activity is partial (e.g., focal) or generalized. In an embodiment, a compound/composition of the present disclosure is used to treat partial and/or generalized seizures.

Partial seizures are considered those in which the seizure activity is restricted to discrete areas of the cerebral cortex. As is known in the art, if consciousness is fully preserved during the seizure, the seizure is considered to be a simple-partial seizure. If consciousness is impaired, the seizure is considered to be a complex-partial seizure. Within these types of seizures are included those that initiate as partial seizures and subsequently extend through the cortex; these are considered partial seizures with secondary generalization.

Generalized seizures encompass distant regions of the brain simultaneously in a bilaterally symmetric manner and can include sudden, brief lapses of consciousness, such as in the case of absence or petit mal seizures, without loss of postural control. Atypical absence seizures usually include a longer period of lapse of consciousness, and more gradual onset and termination. Generalized tonic-clonic or grand mal seizures, which are considered to be the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 seconds, the tonic phase of the seizure typically evolves into the clonic phase, produced by the superimposition of periods of muscle relaxation on the tonic muscle contraction. The periods of relaxation progressively increase until the end of the ictal phase, which usually lasts no more than one minute. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 seconds. Consciousness is briefly impaired, but there is usually no postictal confusion. Myoclonic seizures are characterized by a sudden and brief muscle contraction that may involve one part of the body or the entire body. It is considered that the present disclosure is applicable for prophylaxis and/or therapy of any of the foregoing types of seizures, which are described for illustration but are not meant to be limiting. In embodiments, the disclosure is pertinent to treatment of epilepsy. In embodiments, the epilepsy is selected from idiopathic, cryptogenic, symptomatic, general and focal epilepsy. In embodiments, the disclosure is pertinent to treatment of pharmacoresistant epilepsy. As used herein, the term pharmacoresistant epilepsy means an epilepsy that is not controlled despite use of at least two drugs that are suitable for the type of epilepsy and have been appropriately prescribed at maximum tolerated doses. In embodiments the pharmacoresistant epilepsy is one where three such drugs trials have failed to eliminate the seizures. Those skilled in the art will recognize that the chances of controlling epilepsy decline sharply after failure of the second or third antiepileptic drug trial, and thus the present disclosure provides an approach designed to address these failed treatment cases.

It will be recognized by those of skill in the art that the form and character of the particular dosing regimen employed in the method of this disclosure will be dictated by the route of administration and other well-known variables, the sex and size of the individual, and the type of seizure disorder being treated.

In embodiments, the disclosure includes administering a composition comprising a therapeutically effective amount of a compound described herein. "Therapeutically effective amount" as used herein means that amount of compound that elicits the biological or medicinal response that is being sought by a medical doctor or other clinician, and includes alleviation of one or more of the symptoms of the disease or disorder being treated, and/or reduction of the severity of one or more of the symptoms of the disease or disorder being treated. In embodiments, the therapeutically effective amount is an amount that is adequate to reduce the severity and/or frequency and/or duration of seizures experienced by the individual. In an embodiment, seizures are terminated or prevented by the administration. The compositions comprising compounds of this disclosure may contain, per unit dosage unit, e.g., tablet, capsule, powder, injection, suppository, topical formulation, ampule, inhalation formulation, teaspoonful and the like, of from about 0.1-1000 mg and may be given at a dosage of from about 0.01-200.0 mg/kg/day. Values of ranges, concentrations, units and the like described herein are inclusive of the upper and lower values, and include all integers and ranges there between to the first decimal point. Combinations of the compounds and other agents, such as other known epileptic drugs, are included in this disclosure.

Compositions comprising the compounds described herein can be administered to an individual using any available method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. Topical and/or transdermal administrations are also encompassed.

In an aspect, the disclosure further provides products, e.g., articles of manufacture, which comprise compositions (e.g., pharmaceutical preparations) comprising any one or any combination of the compounds and/or compositions described herein. The articles are, for example, kits comprising a composition and directions for its use.

In an embodiment, the product is a closed or sealed package that contains the compound(s) and/or composition(s) (e.g., pharmaceutical preparation(s)). In certain embodiments, the package can comprise one or more closed or sealed vials, bottles, blister (bubble) packs, or any other suitable packaging for the sale, or distribution, or use of the compound(s) and/or composition(s). The printed material can include printed information. The printed information can be provided on a label, or on a paper insert, or printed on the packaging material itself. The printed information can include information that identifies the compound in the package, the amounts and types of other active and/or inactive ingredients, and instructions for taking the compound(s) and/or composition(s), such as the number of doses to take over a given period of time, and/or information directed to a pharmacist and/or another health care provider, such as a physician, or a patient. The printed material can include an indication that the compound(s) and/or composition(s) and/or any other agent provided with it is for treatment of seizures, tremors, and/or any disorder associated with seizures and/or tremors. In embodiments, the product includes a label describing the contents of the container and providing indications and/or instructions regarding use of the contents of the container to treat any seizure or seizure disorder. In an embodiment, the disorder is epilepsy. In embodiments, the epilepsy is idiopathic, cryptogenic, symptomatic, generalized, focal, or partial.

The following specific examples are provided to illustrate the invention, but are not intended to be limiting in any manner.

Example 1

This example provides a description of compounds of this disclosure and methods for their synthesis. In this regard, a class of para-substituted N-phenyl enaminones possessing a sulfonamide bridge (Series 1) and a benzamide bridge (Series 2) was synthesized to evaluate the analogs efficacy against partial seizures in the 6 Hz rodent model and generalized seizures in the MES rodent model, as well as in a corneal focal model.

Figure 2:
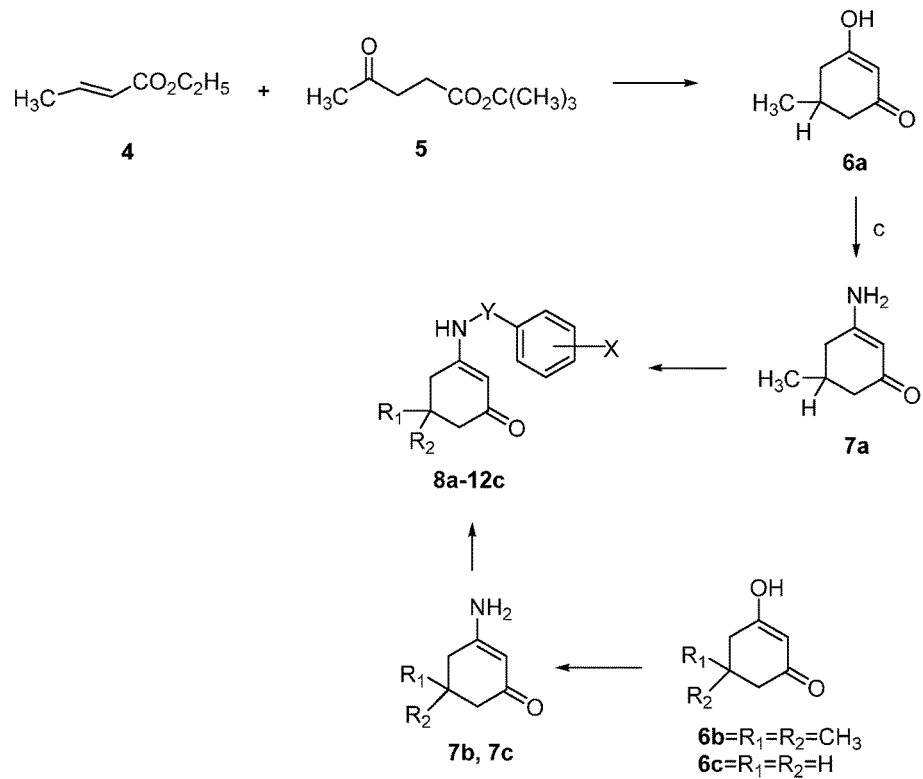
FIG. 2 provides a general synthetic scheme for synthesis of compounds of this disclosure.

Synthesis. The N-phenyl sulfonamide 2 and benzamide 3 enaminones were synthesized by amination of the respective β-diketones, followed by N-sulfonylation or N-acylation of the enaminone intermediates with corresponding aromatic sulfonyl or acyl chlorides in a base-catalyzed reaction, as shown in Scheme 1, shown in FIG. 2. The first step condensation reaction for the 5-methyl enaminone intermediate (7a): involves the condensation of ethyl crotonate (4) with tert-butyl acetoacetate (5), under basic conditions to produce the tert-butyl ester 5-methylcyclohexane-1,3-dione. The 5-methyl-1,3-cyclohexanedione (6a) was synthesized by an acidic catalyzed ester hydrolysis and decarboxylation reaction of the diketo tert-butyl ester before conversion to the enaminone intermediate, (7a). The second step amination procedure: the mono methyl diketone (6a) was treated with ammonium acetate to give the desired enaminone intermediate (7a). A Dean-Stark trap was used for azeotropic distillation to remove the water during refluxing. The final step sulfonylation reactions and acylation reaction: Due to the poor nucleophilicity of the enaminone system (vinylogous amide) a strong base (e.g., sodium hydride) was required for N-deprotonation. Sulfonylation of the amino anion (7a) was achieved with the corresponding para-substituted aromatic sulfonyl chlorides to generate the desired sulfonamide enaminones (Y=SO$_2$) 8a-c, 9a-c, and 10a-c. Where 8a-c, X=OCF$_3$; 9a-c, X=CH$_2$Ph; 10a-c, X=CF$_3$. Acylation of the amino anion (7a) was achieved with the corresponding para-substituted aromatic acid chlorides to generate the desired benzamide (Y=CO) 11a-c and 12a-c. Where, 12a-c, X=OCF$_3$; and 11a-c, X=CF$_3$. The diketones, 5,5-dimethyl-1,3-cyclohexanedione (7b) and 1,3-cyclohexanedione (7c), are commercially available. For generating the target compounds (8a-12c), the diketones (6b-c) underwent the same synthetic procedures for the amination reaction, and for the base-catalyzed sulfonylation and acylation reactions as previously discussed. TLC analysis was used to monitor reaction progress. Synthetic conditions for the cyclic enaminone intermediates 7a-c are well established and successful. All synthesized analogs (FIG. 1) were structurally identified by proton Nuclear Magnetic Resonance (NMR) and elemental analyses.

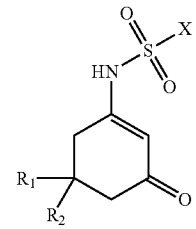

2

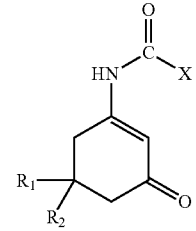

3

General Procedure for N-phenyl Sulfonamide Enaminone Derivatives. Melting points (mp) were determined on a ThermoFisher digital capillary melting point apparatus and were uncorrected. The $^1$H spectra were recorded on a Bruker 1 Ultra Shield-400 MHz NMR spectrometer. The samples were dissolved in deuterated dimethylsulfoxide (DMSO-d$_6$). Elemental analyses (C, H, N, S and halogen) were performed by NuMega Labs, San Diego, Calif., USA. The analytical results for the elements were within ±0.4% of the theoretical values. Starting materials, cyclohexane-1,3-dione, 5,5-dimethylcyclohexane-1,3-dione, and the para-substituted benzene sulfonyl chloride reagents were obtained from Sigma-Aldrich Chemical Company, Milwaukee, Wis., USA and used without further purification. 5-Methylcyclohexane-1,3-dione (6a), 3-amino-5-methylcyclohex-2-enone (7a) 3-amino-5,5-dimethylcyclohex-2-enone (7b), and 3-aminocyclohex-2-enone (7c) were all prepared by literature methods.

General synthetic procedure for the preparation of 3-para-substituted benzenesulfonylamino 5-methyl enaminones. Compounds 8a, 9a, and 10a. Into a 500 mL three-neck round bottom flask equipped with a condenser, pressure-equalizing dropping funnel, and magnetic stirrer was added anhydrous tetrahydrofuran (THF). After cooling on an ice bath, sodium hydride (2.8 equiv)) was added; followed by additional dry THF. 3-Amino-5-methylcyclohex-2-enone (7a) (1 equiv) was added followed by dry THF. The reaction mixture was allowed to reflux for 1 hour. Once cooled to room temperature, the mixture was placed on an ice bath for 5 min before adding para-substituted benzenesulfonyl chloride (1 equiv) in 30 mL of dry THF dropwise. The reaction mixture was refluxed for 1 hour. Once cooled to room temperature the mixture was quenched with deionized (DI) water and acidified with concentrated HCl. The aqueous solution was extracted with dichloromethane (and the organic layer washed with water. The organic phase was dried over $MgSO_4$, filtered, and evaporated in vacuo at a temperature not exceeding 35° C. The crude residue was taken up with a minimum amount of methylene chloride and chromatographed on a silica gel column using v/v EtOAc/Hexane (9:1) as the eluted solvent mixture. Fractions containing the target compound were concentrated in vacuo to yield a yellowish-white semi-solid residue that was triturated with anhydrous $Et_2O$. The white precipitate was collected via vacuum filtration. Mp, CHNS, and $H^1$ NMR was determined for each compound.

General synthetic procedure for the preparation of 3-para-substituted benzenesulfonylamino enaminones. Compounds 8b, 9b, and 10b. Into a 250 mL two-neck round bottom flask fitted with a pressure-equalizing dropping funnel and magnetic stirrer was added anhydrous tetrahydrofuran (THF). After 5 min of cooling, sodium hydride (2.8 equiv) was cautiously added along with dry THF. 3-Aminocyclohex-2-enone (7c) (1 equiv) was added over 30 min with continuous stirring. The reaction mixture was allowed to reflux for 1 hour. Once cooled to room temperature, the mixture was placed on an ice bath for 5 min before adding para-substituted benzenesulfonyl chloride (1 equiv) dropwise. The reaction mixture was refluxed for 1 hour and monitored by TLC. Once cooled to room temperature the reaction was quenched with DI water and neutralized with concentrated HCl. The aqueous solution was extracted with dichloromethane and the organic layer washed with water. The organic phase was dried over $MgSO_4$, filtered, and evaporated in vacuo at a temperature not exceeding 35° C. The crude residue was taken up with a minimum amount of methylene chloride and chromatographed on a silica gel column using v/v EtOAc/Hexane (9:1). Fractions containing the desired product were concentrated in vacuo and the residue was triturated with anhydrous ether ($Et_2O$). The white crystals remaining were collected via vacuum filtration and characterized. Mp, CHNS, and $H^1$ NMR was determined for each compound.

General synthetic procedure for the preparation of 3-para-substituted benzenesulfonylamino 5,5-dimethyl enaminones. Compounds 8c, 9c, and 10c. To a 250 mL three-neck round bottom flask fitted with a condenser, pressure-equalizing, rubber septum, and magnetic stirrer, anhydrous THF was added and allowed to cool for 5 min on an ice bath. Sodium hydride (2.8 equiv) was added along with dry THF. After 5 min, 3-amino-5,5-dimethylcyclohex-2-enone (7b) (1 equiv) was added along with THF and the mixture refluxed for 20 min. Once cooled to room temperature the mixture was placed on an ice bath for 5 min before a solution of para-substituted benzenesulfonyl chloride (1 equiv) in dry THF was added dropwise. After stirring at room temperature for 10 min, the mixture was quenched with of DI water and transferred to a 500 mL Erlenmeyer flask. Concentrated HCl was slowly added followed by extraction with dichloromethane. The organic layer was washed with water. The organic phase was dried over $MgSO_4$, filtered, evaporated in vacuo and washed twice with 100 mL of anhydrous ether. The residue was purified by column chromatography (9:1 v/v EtOAc: MeOH). Fractions containing desired product were evaporated in vacuo, recrystallized and characterized. Mp, CHNS, and $^1H$ NMR was determined for each compound.

General Procedure for N-phenyl Benzamide Enaminone Derivatives. General procedure for the preparation of 3-para-substituted N-benzamide mono-methyl, 5,5-dimethyl, and unsubstituted enaminones. Compounds 11a-12c. To a 250 mL two-neck round bottom flask fitted with a magnetic stirrer and under nitrogen, 20 mL of THF was added. The reaction flask was placed on an ice bath and stirred. After cooling for at least 5 minutes, sodium hydride (2 equiv) was added, followed by 20 mL of THF. Next, the enaminone intermediate (7a, 7b, or 7c) (1 equiv) was added to the flask over 5 minutes, followed by 15 mL of THF. The flask was brought back to room temperature and fitted with a condenser to reflux for 20 minutes at room temperature. Upon reflux, the reaction flask was placed back in the ice bath and allowed to cool for at least 5 minutes. Prior to the addition of the corresponding benzoyl chloride, the reagent was mixed with THF and placed in a dropwise apparatus. The mixture stirred for 20 minutes at room temperature. After confirmation of reaction completion, the reaction was quenched with DI $H_2O$ and 8 mL concentrated HCl. The contents of the flask were added to a 500 mL separatory funnel and organic extraction was performed using dichloromethane. The organic layer was collected and washed with $NaHCO_3$ (sat. aq.) and 50 mL of DI $H_2O$. The organic phase was transferred to a 500 mL flask and dried with $MgSO_4$. The product sat overnight, and then collected via vacuum filtration. Mp, CHN, and $H^1$ NMR was determined for each compound.

Example 2

This example provides a demonstration of the efficacy of the present compositions for use in prophylaxis and/or therapy of seizure disorders using several distinct, clinically relevant animal models.

Pharmacological testing of the synthesized compounds was conducted. Four initial screenings were performed: Phase I, Phase II, Phase VIA, and Phase VIB. These testing procedures have been previously described and are known in the art. Phase I and Phase VI A evaluations of the sulfonamide enaminones included four tests: maximal electroshock (MES), subcutaneous pentylenetetrazol (scPTZ), 6 Hz psychomotor, and rotorod neurotoxicity (Tox) in mice. The electrical induced 60 Hz (50 mA in mice and 150 mA in rats via corneal electrodes) MES test is a model used to identify compounds with the ability to prevent seizure spread. This model mimics behavioral and electrographic generalized tonic-clonic seizures in humans. The chemically induced scPTZ seizure type model identifies compounds that inhibits the seizure effects of pentylenetetrazol or raise the seizure threshold. The alternative low-frequency (32 mA), long duration (3s) electroshock 6-Hz seizure model identify compounds that are active against partial seizures and/or therapy-resistant epilepsy. Finally, the neurotoxicity test detects toxicity in mice according to the rotorod test. Neurological impairment can be confirmed by the mouse's inability to maintain equilibrium on the rotorod for one minute. If the animal falls off the rotorod three times during a one minute period, the animal is considered to be experiencing neurotoxicity. The test compounds were grounded with a mortar and pestle to make the suspension (compounds were suspended in 0.5% aqueous methylcellulose) followed by a 10 minute incubation in a sonabath (sonicator). The route of administration was by intraperitoneal injection (ip) at three dosage levels (30, 100, and 300 mg/kg), with anticonvulsant activity and motor impairment noted at 15 minute, 30 minute, 1, 2, and 4 hours after administration. Phase II testing quantited the administration of anticonvulsant activity and motor impairment observed for the most promising compounds in Phase I. Thus, the median effective dose ($ED_{50}$) and the median toxic dose ($TD_{50}$) were determined in this analysis. Phase I and Phase II test were carried out in male Carworth Farms no. 1 (CF1) mice. Phase VIA provided oral (po) rat data comparable to Phase I ip data in mice, while Phase VIB quantitated these results in a manner identical to the Phase II data in mice. Male Sprague-Dawley rats were employed for these evaluations. For analogues inactive in the mice MES and scPTZ tests, they underwent further screening in the 6 Hz psychomotor seizure analysis. Similar to Phase I screening procedures, mice were pretreated ip with 100 mg/kg of the test compounds and at various time intervals (0.25, 0.5, 1, 2, 4, and 6 hours) post administration, the mice (four at each time point) were subjected to a low frequency electrical current to produce a 'psychomotor' seizure. Animals not showing a behavioral change were considered protected. For the anticonvulsant and toxicity screening, the results for each time interval were expressed as a ratio of the number of animals protected or toxic over the number of animals tested.

Pharmacological testing of the compounds listed in Table 1 was performed. As described above all compounds underwent Phase I evaluation in four mice models: 1) maximal electroshock seizure (MES), 2) subcutaneous Metrazol (sc Met), 3) 6 Hz psychomotor, and 4) neurologic toxicity (Tox) at different time intervals (0.5h-8h) and different doses ranging from 30-300 mg/kg. All analyses were performed on groups of four or more mice. The MES and sc Met tests have become the two most widely employed preclinical seizure models for the early identification and high throughput screening of investigational antiepileptic drugs. These tests, albeit extremely effective in identifying new antiepileptic drugs that may be useful for the treatment of human generalized tonic-clonic seizures and generalized myoclonic seizures, may miss novel antiepileptic drugs that could be useful for the treatment of therapy-resistant partial seizures. In light of this observation, investigational compounds found to be inactive in either the MES or sc MET tests were also screened for their ability to block psychomotor seizures induced by a low-frequency (6 Hz) 32 mA, long-duration (3 sec) stimulus delivered through corneal electrodes. Stimulation may also be increased to 44 mA. Phase I data for the sulfonamides and benzamides enaminones are shown in Table 1. All compounds showed moderate to good anticonvulsant activity mainly in the 6 Hz and MES animal models. The 6 Hz activity is novel for this class of compounds. Thus, in embodiments, the present disclosure relates to compounds that are active in the 6 Hz model. In certain embodiments the compounds are active in the 6 Hz model, but not active in one or a combination of other models described herein.

Four of the most active lead compounds in the MES generalized seizure model and the 6 Hz therapy-resistance partial seizure model, shown in Table 1, are described for illustrative purposes. Three of compounds (11b, 11c, and 12c) showed good 6 Hz (32 mA) activity protecting animals (25% or above) at the standard dose of 100 mg/kg with early onset (0.25 h) and long to moderate duration of action. Compound 12b is the most potent compound, protecting animals (50% tested) at 30 mins at a low dose of 30 mg/kg. Compound 10a 6 Hz results are minimal but show protection in 25-75% of animals in the MES model, having prolonged duration of action up to 4 hours. All compounds possess limited to no observed neurobehavioral toxicity effects at each tested dose. As a common trend, the pre-clinical pharmacological profiles of several active compounds were found to be similar to the current AEDs, phenytoin (MES and scPTZ active only) and levetiracetam (6 Hz active only).

TABLE 1

Anticonvulsant MES, sc MET and 6 Hz Screening Results.

| ID (ADD)[a] | MES[b] (%) of animals protected | scMET[b] (%) of animals protected | 6 Hz (32 mA) Psychomotor (%) of animals protected | Neurotoxicity[c] |
|---|---|---|---|---|
| 8a | | | | |
| 8b (ADD 443020) | Class II 100 mg/kg @ 4 h (25%) | Class III | No Activity | NT |
| 8c (ADD 442005) | Class II 100 mg/kg @ 2 h (25%) 4 h (25%) | Class III | Tested @ 100 mg/kg Protection at: 1.0 h (25%) | NT |
| 9c (ADD 442004) | Class II 100 mg/kg @ 2 h (25%) | Class III | Tested @ 100 mg/kg Protection at: 1.0 h (25%) | NT |
| 10a (ADD 442006) | Class II 100mg/kg @ 1 h (25%) 2 h (50%) 4 h (75%) | Class III | Tested @ 100 mg/kg Protection at: 0.50 h (25%) | NT[d] |
| 10b (ADD 458041) | Class II 100 mg/kg @ 2 h (75%) 300 mg/kg @ 2 h (100%) | — | No Activity | NT |

TABLE 1-continued

Anticonvulsant MES, sc MET and 6 Hz Screening Results.

| ID (ADD)[a] | MES[b] (%) of animals protected | scMET[b] (%) of animals protected | 6 Hz (32 mA) Psychomotor (%) of animals protected | Neurotoxicity[c] |
|---|---|---|---|---|
| 10c (ADD 458042) | Class II 100 mg/kg @ 2 h (25%) 300 mg/kg @ 2 h (50%) | — | Tested @ 300 mg/kg Protection at: 0.50 h (50%) | 300 mg/kg ⅛ animals @ 0.5 h ⅔ animals @ 2 h |
| 11a ADD (458043) | Class II 300 mg/kg @ 0.5 h & 2 h (25%) | — | Tested @ 300 mg/kg; Protection at 0.5 h (100%) 2 h (100%) | NT |
| 11b (ADD 445009) | Class III in mice Class I in rat protected 25% @ 0.5 h @ 30 mg/kg | Class II 100 mg/kg @ 0.5 h (25%) (myoclonic jerks) in mice | Tested @ 100 mg/kg; Protection at 0.25 h(25%), 0.5 h (50%), 1 h (50%) 2 h (25%), 4 h (25%) | Toxicity @ 1 h & 2 h in mice. 6 HZ-25% animals @ 1 h. minor tox |
| 11c (ADD 445008) | Class III | Class III | Tested @ 100 mg/kg; Protection at 0.25 h (25%) 0.5 h (50%) 1.0 h (25%) | NT |
| 12a ADD (464002) | No activity | — | Tested @ 100 mg/kg @ 30 min 25% of animals were protected. 300 mg/kg @ 30 min 50% of animals were protected. | NT |
| 12b ADD (464003) | Class II 300 mg/kg @ 2h 75% of animals protected | — | Tested 30 mg/kg @ 30 min 50% of animals were protected. 100 mg/kg @ 30 min and 2 h 50% of animals were protected. 300 mg/kg @ 30 min 75% and 2 h 50% of animals were protected. | 25% animals at 100 mg/kg and 37% animals at 300 mg/kg |
| 12c ADD (464001) | No activity | — | Tested @ 100 mg/kg @ 30 min and 2 h 75% of animals were protected. 300 mg/kg @ 30 min and 2 h 100% of animals were protected. | 25% animals at 300 mg/kg |

[a]Anticonvulsant Drug Development identification number;
[b]Phase I in mice activity - Class I = activity at 100 mg/kg or less; Class II = activity between 100 and 300 mg/kg; Class III = no activity at 300 mg/kg; Class IV = activity was inconsistent;
[c]Non-toxic;
[d]Test subjects experienced diarrhea at 100 mg/kg at 0.5 hour;

It will be apparent from the foregoing that four ADDs 445009 (11c), 445008 (11b), 464003 (12b), and 464001 (12c) all showed to be most efficacious in the 6 Hz partial seizure model with little to no neurotoxicity.

We tested two of these compounds (for compounds 11b (ADD 445009) and 11c (ADD 445008)) in the well-known corneal kindled (focal seizure) mouse model). The corneal kindled model is an advanced model that identifies compounds that prevent focal seizures (Stage 5 seizures, facial clonus and head nodding progressing to forelimb clonus, and finally rearing and falling accompanied by a generalized clonic seizure) in kindled mice after dosing. Treated animals not displaying a Stage 3, 4, or 5 seizure are considered protected. The dose of the test substance was varied between the limits of 0 and 100% efficacy. Compound 11b had 100% efficacy (4 out of 4 animals tested were protected) at 100 mg/kg at 1.0 hour, having an overall average seizure score of 1.0. Compound 11c, also was very efficacious protecting 100% of animals (4 out of 4 animals tested) at 30 minutes, which is an earlier onset of activity, and having a perfect average seizure score of zero.

TABLE 2

Corneal Kindling (Focal Seizure) Mouse Model Results.

| Compound | Dose (mg/kg) | Time (hrs) | Number of animals protected/Number of animals tested | Individual Seizure Scores | Average Seizure Score |
|---|---|---|---|---|---|
| 11b (ADD 445009) | 100 | 1.0 | 4/4 | 2, 0, 0, 2 | 1.0 |
| 11c (ADD 445008) | 100 | 0.5 | 4/4 | 0, 0, 0, 0 | 0.0 |

While the invention has been described through specific embodiments, routine modifications will be apparent to those skilled in the art and such modifications are intended to be within the scope of the present invention.

What is claimed is:
1. A compound having the following structure:

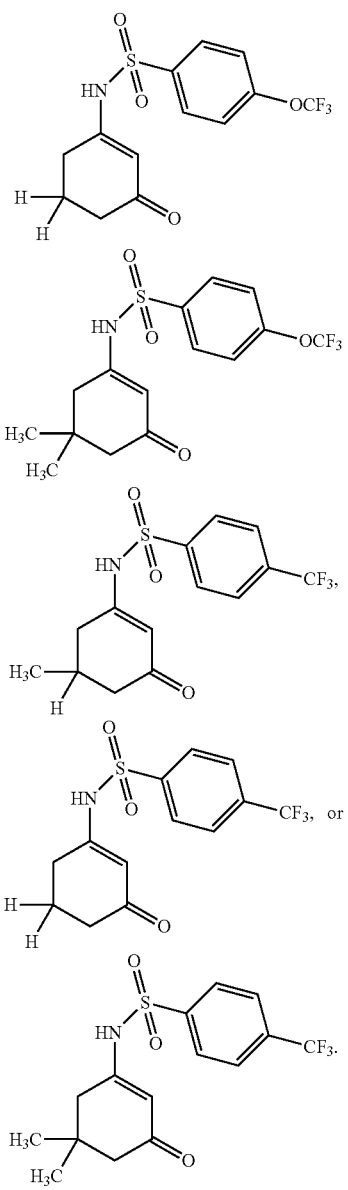

2. The compound of claim 1, wherein the compound has the following structure:

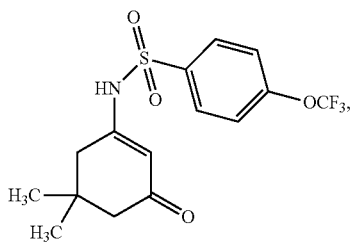

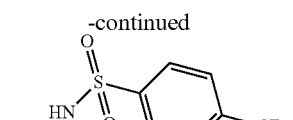

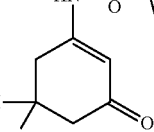

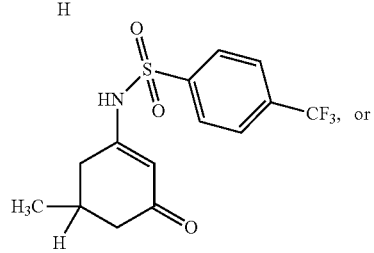

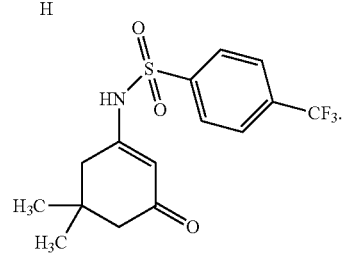

3. A composition comprising a compound of claim 1 and a pharmaceutically acceptable carrier.

4. A method for treating a seizure in an individual in need thereof comprising administering to the individual a composition comprising a therapeutically effective amount of a compound of claim 1.

5. The method of claim 4, wherein the seizure is an epileptic seizure.

6. The method of claim 4, wherein the seizure is a partial seizure.

7. The method of claim 4, wherein the seizure is a generalized seizure.

8. The method of claim 4, wherein the individual in need has previously experienced an epileptic seizure.

9. An article of manufacture comprising packaging and at least one container, wherein the container contains a composition comprising a compound of claim 1, the article further comprising printed material, the printed material providing an indication that the composition is for use in treatment of a seizure disorder.

10. The article of claim 9, wherein the seizure disorder is epilepsy.

11. The article of claim 9, wherein the seizure disorder comprises partial seizures.

12. The article of claim 9, wherein the seizure disorder comprises generalized seizures.

13. The compound of claim 1, wherein the compound is active in at least in therapy resistance psychomotor (6-Hz) model.

* * * * *